(12) United States Patent
Chen-Yang et al.

(10) Patent No.: US 8,574,498 B2
(45) Date of Patent: Nov. 5, 2013

(54) BIOCHIP WITH A THREE-DIMENSIONAL MESOPOROUS LAYER

(75) Inventors: Yui-Whei Chen-Yang, Tao-Yuan (TW);
Jui-Chuang Wu, Tao-Yuan (TW);
Yen-Kuang Li, Tao-Yuan (TW);
Huan-Ching Yang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 27 days.

(21) Appl. No.: 13/336,786

(22) Filed: Dec. 23, 2011

(65) Prior Publication Data
US 2012/0107192 A1    May 3, 2012

Related U.S. Application Data

(62) Division of application No. 11/623,120, filed on Jan. 15, 2007, now Pat. No. 8,394,323.

(30) Foreign Application Priority Data

Jul. 14, 2006  (TW) ................................ 95125769 A (51) Int. Cl.
*G01N 15/06* (2006.01)
(52) U.S. Cl.
USPC ........................................................ 422/68.1
(58) Field of Classification Search
USPC ........................................................ 422/68.1
See application file for complete search history.

(56) References Cited

U.S. PATENT DOCUMENTS

| 6,951,682 B1 | 10/2005 | Zebala |
| 2003/0022524 A1 | 1/2003 | Smith et al. |
| 2003/0129740 A1 | 7/2003 | Seo et al. |

*Primary Examiner* — Lore Jarrett
(74) *Attorney, Agent, or Firm* — WPAT, PC; Justin King (57) ABSTRACT

The present invention discloses a biochip comprising a substrate and a three-dimensional mesoporous layer on top of it, wherein the mesoporous layer on top is chemically modified to recognize labeling DNAs, proteins, peptides, saccharides, and cells. In addition, this invention also discloses a method for forming the biochip with a three-dimensional mesoporous layer, including a blending process, a heating process, a coating process, a gelation process, a drying process, and a surface modification process.

9 Claims, 8 Drawing Sheets

BIOCHIP WITH A THREE-DIMENSIONAL MESOPOROUS LAYER

CROSS REFERENCE TO RELATED APPLICATIONS

This is a divisional of U.S. Ser. No. 11/623,120, filed Jan. 15, 2007 by the same inventors, and claims priority there from. This divisional application contains rewritten claims to the restricted-out subject matter of original claims.

BACKGROUND OF THE INVENTION

1. Field of the Invention

The present invention is generally related to a biochip, and more particularly to a biochip with a three-dimensional mesoporous layer and a method for forming the same.

2. Description of the Prior Art

At present, the biochip detection technology becomes increasingly important in biotechnology. The biochip detection technology can simultaneously detect various pathogens on a single chip and break the detection limitation achieved by traditional technologies. A microarrayed biochip is generally prepared by aligning a large quantity of bio-probes (DNA's or proteins) on a chip substrate and is used for analyzing or testing samples by the hybridization of DNA-DNA or specific binding between proteins. According to the detection objectives, there are two major categories for microarrayed biochips: DNA chip and protein chip. DNA chips use nucleotide molecules as the probes to detect their nucleotide fragments. DNA chips can also be categorized into complimentary DNA (cDNA) chips and oligonucleotide chips, according to the length of the probes spotted on chips. cDNA chips are often used in the research of gene expressions; while oligonucleotide chips can also be used in diagnosis of pathogen and genotyping in addition to gene expression analysis.

For DNA chips, probes are immobilized on substrates and used to detect specific DNA fragments by the characteristic hybridization with complimentary DNA's.

DNA chips can be applied on disease detection and shorten the time for developing new medicines. DNA chip is also a powerful tool for analyzing DNA's by appropriate dye labeling in visible emission lights. By different emission wavelengths, individual target DNA can be distinguished and analyzed.

The improvement of detection sensitivity by modifying the substrate surfaces of traditional biochips is currently still being sought to obtain amplified signals to facilitate further analysis. Thus, a novel biochip preparation method is proposed to achieve the high-sensitivity performance.

SUMMARY OF THE INVENTION

In accordance with the present invention, a biochip with a three-dimensional mesoporous layer and a method for forming the same are provided.

The three-dimensional mesoporous material is a network polymer with nano-scaled pores, such as aerogel material. Its porosity can be as high as 95%. Due to its high porosity, it possesses a variety of characteristics: high specific surface area, low density, low heat conductivity, low sound spreading speed, low dielectric constant, and so forth. Therefore, it can be applied in various fields, such as heat insulation, catalyst, adsorbent, electrodes, electronics, detectors, etc.

The first objective of the present invention is to synthesize materials on the top of a flat substrate to form a three-dimensional mesoporous layer using the sol-gel technique.

The second objective of the present invention is to utilize the large three-dimensional inner specific surface area to recognize labeled DNAs, proteins, peptides, saccharides, and cells. Thus, the biochip with a three-dimensional mesoporous layer according to the present invention has the characteristics of high sensitivity of detection so as it would have a potential to simplify the detection equipments. For example, only data type camera (CCD) would be required instead of complicated imaging technique. Therefore, this present invention does have the economic potential for industrial applications.

Accordingly, the present invention discloses a biochip comprising a substrate and a three-dimensional mesoporous layer on top of the substrate. The surface of the three-dimensional mesoporous layer is chemically modified to recognize labeled DNAs, proteins, peptides, saccharides, and cells. In addition, this invention also discloses a method for preparing the biochip with a three-dimensional mesoporous layer, including a blending process, a heating process, a coating process, a gelation process, a cleaning process, a drying process, and a surface modification process.

DESCRIPTION OF THE PREFERRED EMBODIMENTS

What is probed into the invention is a biochip with a three-dimensional mesoporous layer and a method for forming the same. Detail descriptions of the structure and elements will be provided as followed in order to make the invention thoroughly understood. The application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail as followed. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a method for forming a biochip with a three-dimensional mesoporous layer is disclosed. At first, a precursor solution is provided. The precursor solution comprises an ionic liquid and at least one alkoxide monomer and/or aryloxide monomer. The ionic liquid is used as a template as well as a solvent. The central element of the alkoxide monomer and/or aryloxide monomer comprises one selected from the group consisting of the following elements: Li, Na, K, Rb, Cs, Be, Mg, Ca, Sr, Ba, Ti, Te, Cr, Cu, Er, Fe, Ta, V, Zn, Zr, Al, Si, Ge, Sn, and Pb. Next, a coating process is carried out to coat the precursor solution on a substrate. The material of the substrate comprises one selected from the group consisting of the following materials: silicon chip, glass, or polymer. The precursor solution also comprises an acidic compound or alkaline compound to catalyze the hydrolysis/polymerization of the alkoxide monomer and/or aryloxide monomer. The method for preparing the precursor solution described as followed: firstly blending the alkoxide monomer and/or aryloxide monomer and the ionic liquid together to form a first mixture; next adding an acidic compound to the first mixture to form a second mixture; and finally adding an alkaline compound to the second mixture to enhance the hydrolysis/polymerization reactions of the alkoxide monomer and/or aryloxide monomer.

After the coating process, a gelation process is carried out by having an alcohol contact with the precursor solution on the substrate so as to form a gel membrane. The temperature of the gelation process ranges from 50° C. to 150° C. Then, a cleaning process is carried out to remove the ionic liquid from the gel membrane by a solvent. The temperature of the cleaning process ranges from 30° C. to 200° C. Following that, a drying process is performed to remove the solvent to form the three-dimensional mesoporous layer. The preferred solvent is the one with a low boiling point (less than or equal to 200° C.). Preferably, the solvent comprises one selected from the group consisting of the following: nitrile, alcohol, ketone, and water. The common composition of the three-dimensional mesoporous layer comprises one selected from the group consisting of the following or any combination: $SiO_2$, $TiO_2$, $V_2O_5$, and $Al_2O_3$. The average pore diameter of the three-dimensional mesoporous layer ranges about 2 nm to 50 nm. The specific surface area is more than or equal to 100 $m^2/g$ and the porosity is 50%~99%. Finally, a surface modification process is carried for the three-dimensional mesoporous layer of the composite membrane, so as to form a biochip with a three-dimensional mesoporous layer.

In the embodiment, the mentioned ionic liquids are room temperature ionic liquids (RTIL's), and is formed by mixing an organic base with a Lewis acid. When the Lewis acid is halogenated acid, it can form a room temperature ionic liquid but will produce halogen acid if reacting with water. Therefore, the halogenated acid is not suitable for the present invention. The Lewis acid used by the present invention is not halogenated acid so as to prepare a stable ionic liquid in water. In a preferred example, the cationic moiety in the organic base is alkyl or aryl group having the following general equation:

in which $R^1$, $R^2$, $R^3$, and $R^4$ are selected according to the following table.

| $R^1$ | $R^2$ | $R^3$ | $R^4$ |
|---|---|---|---|
| $CH_3$ | H | $CH_3$ | H |
| $C_2H_5$ | H | $CH_3$ | H |
| $C_2H_5$ | H | $C_2H_5$ | H |
| $CH_3CH_2CH_2CH_2$ | H | $CH_3$ | H |
| $(CH_3)_2CHCH_2$ | H | $CH_3$ | H |
| $CH_3CH_2CH_2CH_2$ | H | $C_2H_5$ | H |
| $CH_3$ | H | $CH_3OCH_2CH_2$ | H |
| $CH_3$ | H | $CF_3CH_2$ | H |
| $CH_3$ | $CH_3$ | $C_2H_5$ | H |
| $CH_3$ | $CH_3$ | $CH_3CH_2CH_2$ | H |
| $C_6H_6CH_2$ | $CH_3$ | $CH_3CH_2CH_2$ | H |
| $C_6H_6CH_2$ | $CH_3$ | $CH_3CH_2CH_2CH_2$ | H |
| $C_6H_6CH_2$ | $CH_3$ | $(CH_3CH_2)(CH_3)CH$ | H |
| $C_6H_6CH_2$ | $CH_3$ | $CH_3CH_2CH_2CH_2CH_2$ | H |
| $CH_3$ | H | $C_2H_5$ | $CH_3$ |
| $C_2H_5$ | H | $C_2H_5$ | $CH_3$ |

For example, the common organic cationic moiety comprises one selected from the group consisting of the following: 1-n-butyl-3-methylimidazolium (BMI), 1-octanyl-3-methylimidazolium (OMI), 1-dodecanyl-3-methylimidazolium (DMI), and 1-hexadecanyl-3-methylimidazolium (HDMI). In addition, the anionic moiety in the Lewis acid comprises one selected from the group consisting of the following: $BF_4^-$, $PF_6^-$, $AsF_6^-$, $SbF_6^-$, $F(HF)_n^-$, $CF_3SO_3^-$, $CF_3CF_2CF_2CF_2SO_3^-$, $(CF_3SO_2)_2N^-$ [TFSI], $(CF_3SO_2)_3C^-$, $CF_3COO^-$, and $CF_3CF_2CF_2COO^-$. When the cationic moiety to be used is determined, the anionic moiety in the Lewis acid can be adjusted to control hydrophilicity/hydrophobicity. For example, BMI-$BF_4$ is hydrophilic and BMI-TFSI is hydrophobic.

For instance, alkyloxide monomer is used as an example. Alkyloxide monomer is hydrolyzed to form hydrophilic silanol (—Si—O—H). Thus, the hydrophilic ionic liquid and silanol are tended to attract to each other and can stabilize the formation of silicon oxide structure so as to obtain more stable three-dimensional silicon oxide mesoporous material. In this embodiment, the weight of the ionic liquid is about 10%~70% weight of the at least alkoxide monomer and preferably about 20%~50%. When the added amount is more than the upper limit, the sol concentration is reduced and the gelation is slow to result in unstable structure.

In this embodiment, when the central element of the alkoxide monomer keeps the same, the specific surface area of the three-dimensional mesoporous material increases with the increase of the molecular weight of the non-alkoxyl block in the alkoxide monomer. For example, in the case of alkoxide monomer, when tetramethyl orthosilicate (TMOS), tetraethyl orthosilicate (TEOS), bis(triethoxysilyl)ethane (BTSE), and bis(triethoxysilyl)benzene (BTSB) are separately used as the precursor, it is found that the specific surface area of the three-dimensional mesoporous material by using BTSE or BTSB is greater than that by using TMOS or TEOS. It is speculated that the increase of the quantities of pores in the three-dimensional mesoporous material as well as the increase of the specific surface area are because the vinyl group of BTSE and the phenyl group of the BTSB occupy the networking space in the three-dimensional mesoporous material.

In this embodiment, the coating process comprises a heating process to heat the precursor solution. The operating temperature of the heating process ranges from 40° C. to 70° C. to form an early stage gel. Besides, the gelation process comprises a gas contacting process and a liquid contacting process. In the gas contacting process, the saturated vapor of the alcohol is in contact with the early stage gel formed by the precursor solution on the substrate to form a stable gel. Following that, in the liquid contacting process the alcohol solution is in contact with the gel layer so as to harden the stable gel layer without shrinkage during the gelation and form said three-dimensional mesoporous layer. The number of carbon atoms in the alcohol is less than or equal to 5.

The modifier for the surface modification process is an alkoxide monomer and/or aryloxide monomer with at least one specific moiety. The specific moiety comprises one selected from the group consisting of the following: amine group, hydroxyl group, carboxyl group, and epoxy group. The common modifier comprises N-[3-(trimethoxysilyl)propyl]-1,2-ethanediamine (DAMO), 3-Glycidoxypropyl-trimethoxysilane (GLYMO), 3-Aminopropyltriethoxysilane (APTS), N-(2-Aminoethyl)-3-aminopropyltriethoxysilane (TMsen) and so forth. According to a preferred example of the present invention, after the surface modification process, a converting process is carried out. At first, a converter that comprises a first moiety and a second moiety is provided. Then, the specific moiety of the modifier is bonded with the first moiety of the converter to form a biochip having the second moiety on its surface. For example, when the modifier is N-[3-(trimethoxysilyl)propyl]-1,2-ethanediamine (DAMO), glutaraldehyde can be used as the converter to form the mesoporous layer having aldehyde group on its surface.

Example

According to a preferred example of the present invention, the method for forming a biochip with a three-dimensional aerogel layer is provided. The method comprises the following steps.

(1) Cleaning a Glass Slide:

The glass slide is rinsed by sodium hydroxide, deionized water and is cleaned in a supersonic oscillation tank. It is then taken out and then dried.

(2) Synthesizing an Aerogel Layer on the Surface of the Glass Slide:

a. Formic acid, ionic liquid (used as the molecular template), and tetraethylsiloxane with a certain ratio are blended and heated to 60° C. by a hot-water bath.

b. The solution in step a is coated onto the surface of the cleaned glass slide by injection. The coated glass slide is placed in a container having saturated ethanol vapor pressure. Then ethanol (its temperature is more than or equal to 60° C.) is added to cover the topmost aerogel layer on the glass slide. It is then stood still for shaping.

c. The slide is then taken out after shaping and rinsed with a low boiling point solvent. After one day, it is taken out and dried.

(3) Modifying the Surface of the Three-Dimensional Aerogel Layer:

N-[3-(trimethoxysilyl)propyl]-1,2-ethanediamine (DAMO) and glutaraldehyde with different concentrations are used as the first type modifier and 3-Glycidoxypropyl-trimethoxysilane (GLYMO) is used as the second type modifier.

Figure 1:
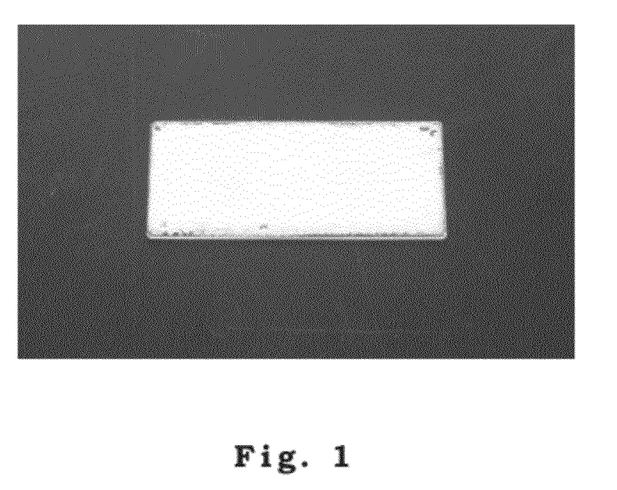
FIG. 1 is a picture showing the slide with a three-dimensional aerogel layer according to a preferred example of the present invention.
Figure 2:
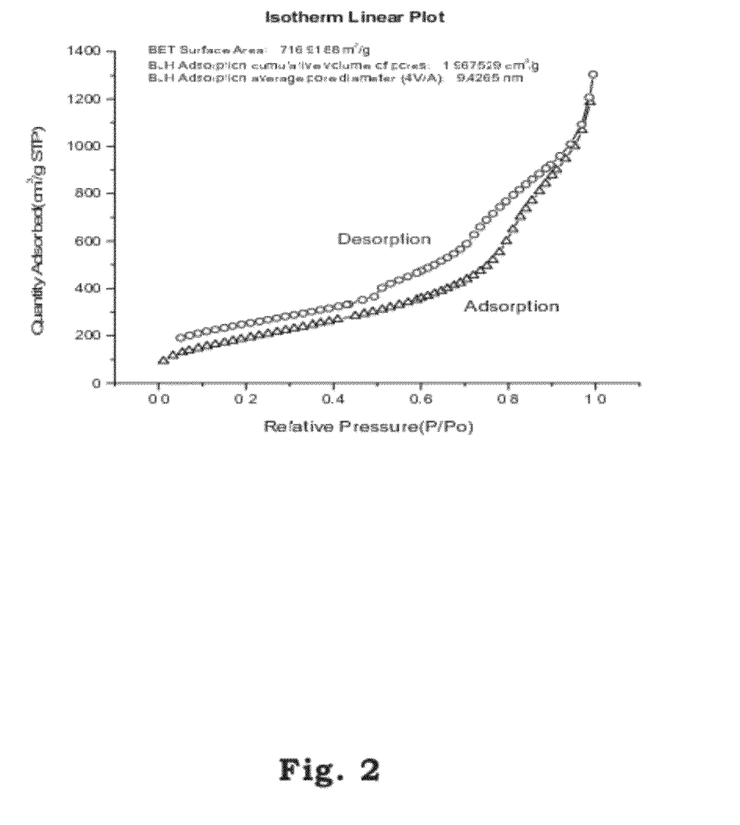
FIG. 2 shows the measurement data of nitrogen adsorption/desorption of the three-dimensional aerogel layer before the modification according to a preferred example of the present invention.

After the above steps (1)~(3), the slide with an aerogel layer is formed. GenePix400B chip scanner is used to scan the background and the fluorescence intensity of the Cy5-labeled Bac-alP1 oligo DNA (60 mer). FIG. 1 shows the outward appearance of the glass slide with the aerogel layer. White powder-like substance is seen on the surface. If clear water is dropped on the glass, it is observed that water diffuses quickly into the inner layer. Referring to FIG. 2, the specific surface area of the unmodified aerogel layer reaches 717 $m^2/g$ and the average pore diameter is 9.4 nm. Porosity is as high as 96% and the volume of the pore is also as high as 2.0 $cm^3/g$.

Figure 3:
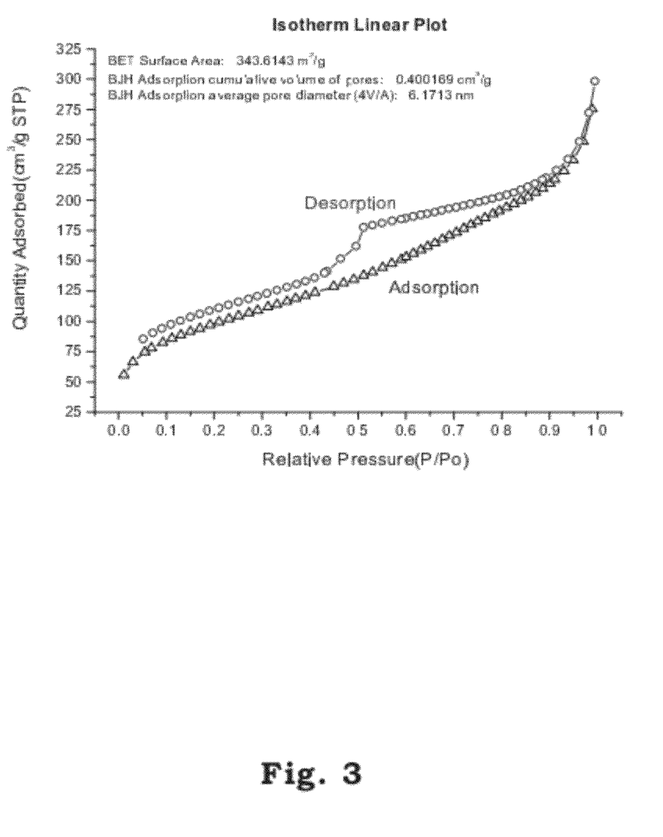
FIG. 3 shows the measurement data of nitrogen adsorption/desorption of the three-dimensional aerogel layer after modified by GLYMO according to a preferred example of the present invention.

FIG. 3 shows the result of the aerogel layer after modified by GLYMO. Its specific surface area is 344 $m^2/g$ and the average pore diameter is 6.1 nm. The volume of the pore is reduced to 0.4 $cm^3/g$. Therefore, the surface modification by GLYMO modifier does not completely block the pores.

Figure 4:
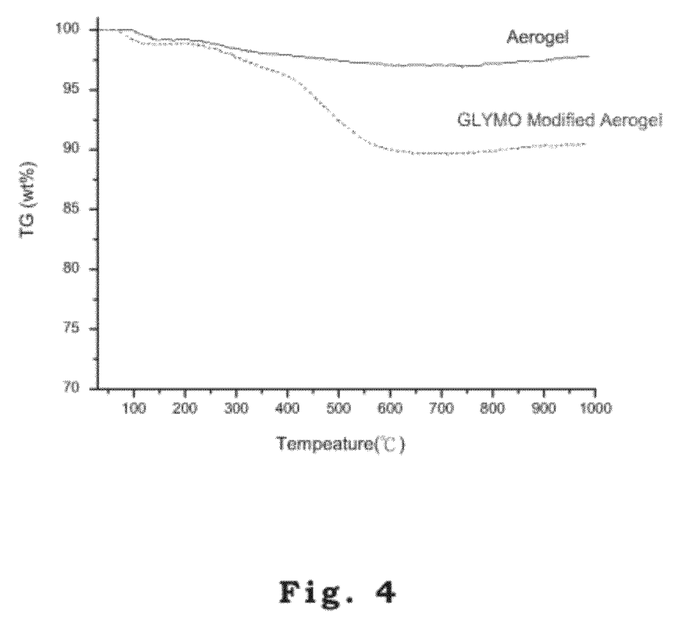
FIG. 4 shows the TGA comparison data of the three-dimensional aerogel layer before/after modification according to a preferred example of the present invention.
Figure 5:
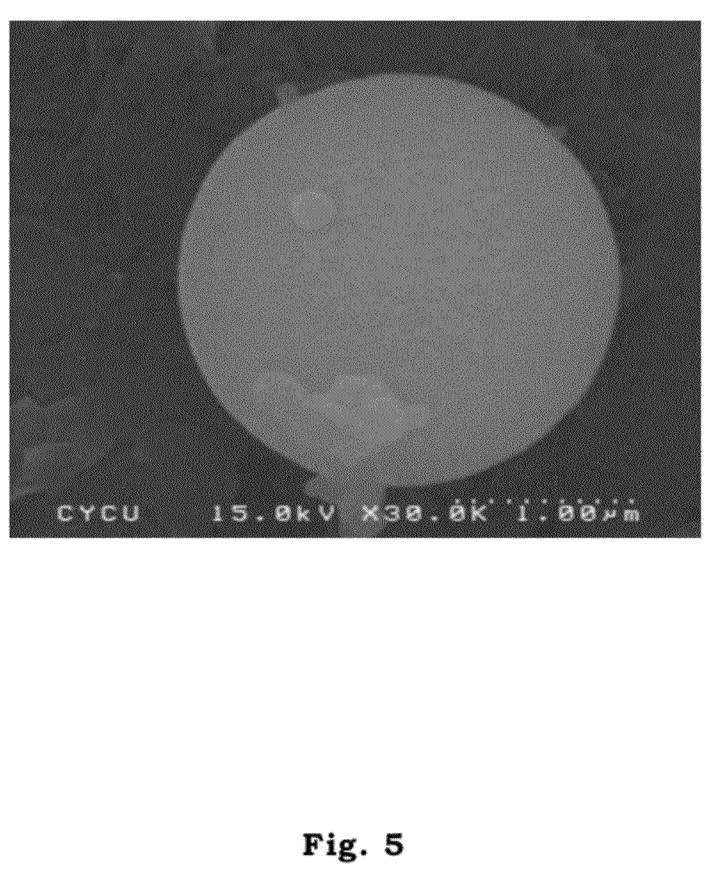
FIG. 5 shows SEM (scanning electron microscope) images of the surface of the three-dimensional aerogel layer according to a preferred example of the present invention.

Referring to FIG. 4, from the thermogravimetric experiment, the weight after modification loses about 15%, compared to that before modification. It indicated that the bonded GLYMO is about 15% weight of the aerogel layer. FIG. 5 shows SEM (scanning electron microscope) image of the surface of the aerogel layer.

Figure 6:
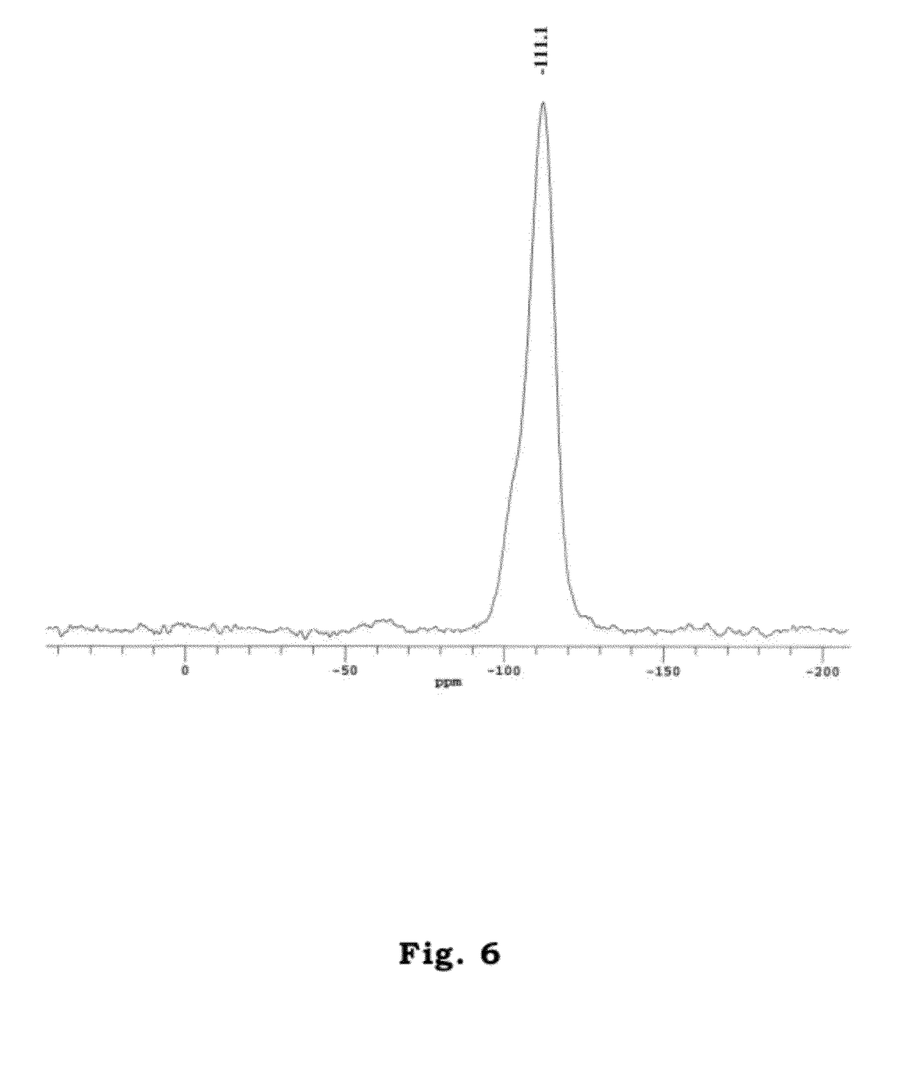
FIG. 6 shows the analysis result of the unmodified three-dimensional aerogel layer according to a preferred example of the present invention by the $^{29}$Si solid-state nuclear magnetic resonance spectrometer.

Referring to FIG. 6, the unmodified three-dimensional aerogel layer has a distinctive peak at −107~−110 ppm, that is the four-substituted silica characteristic peak of the $^{29}Si$ solid-state nuclear magnetic resonance spectrum. As shown in FIG. 6, the major distinctive peak appears around −111.1 ppm, that represents four-substituted Si ($Q_4$), and the rest peak around −100 ppm represents three-substituted Si ($Q_3$), so as to form silica network crosslinking structure.

Figure 7:
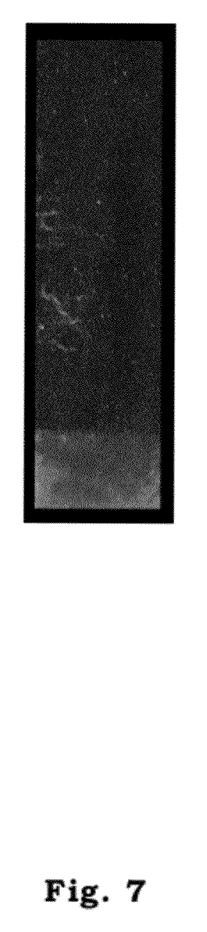
FIG. 7 is a scanned image of the three-dimensional aerogel layer modified by 10% GLYMO according to a preferred example of the present invention.
Figure 8:
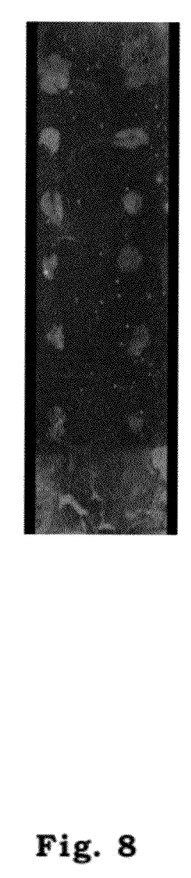
FIG. 8 is a scanned image of the three-dimensional aerogel layer modified by 10% GLYMO and then dripped with Cy5-labeled Bac-alP1 oligo DNA according to a preferred example of the present invention.

FIG. 7 is a scanned image of the three-dimensional aerogel layer modified by 10% GLYMO. From the observed blue uniform signal, the background interference caused by the aerogel layer on the glass slide is very small. FIG. 8 is a scanned image of the aerogel layer modified by 10% GLYMO and then dripped with Cy5 labeled Bac-alP1 oligo DNA. It is found that Cy5 fluorescein shows in light blue circular dots.

Other modifications and variations are possibly developed in light of the above demonstrations. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A biochip with a three-dimensional mesoporous layer, comprising: a substrate covered with a three-dimensional mesoporous aerogel layer, wherein said three-dimensional mesoporous aerogel layer is formed by coating a precursor solution that comprises an ionic liquid and at least one alkoxide monomer and/or aryloxide monomer and then performing a gelation process where the precursor solution comprises the ionic liquid about 20~50 wt % of the at least one alkoxide monomer and/or aryloxide monomer;

the surface of said three-dimensional mesoporous aerogel layer is modified by a modifier that is an alkoxide monomer and/or aryloxide monomer with at least one specific moiety;

said specific moiety comprises one selected from the group consisting of the following: amine group, hydroxyl group, carboxyl group, and epoxy group;

a converter having a first moiety and a second moiety is linked with the specific moiety so as to have the surface of said three-dimensional mesoporous layer having the second moiety;

wherein the substrate is silicon chip, glass, or polymer; and the porosity of said three-dimensional mesoporous layer ranges about 50% to 90%.

2. The biochip according to claim 1, wherein the specific surface area of said three-dimensional mesoporous aerogel layer is more than or equal to 100 $m^2/g$.

3. The biochip according to claim 1, wherein the average pore diameter of said three-dimensional mesoporous aerogel layer is less than or equal to 20 nm.

4. The biochip according to claim 1, wherein the specific surface area of said three-dimensional mesoporous aerogel layer is 344 $m^2/g$.

5. The biochip according to claim 1, wherein the average pore diameter of said three-dimensional mesoporous aerogel layer is 6.1 nm.

6. The biochip according to claim 1, wherein the converter is glutaraldehyde and the modifier is N-[3-(trimethoxysilyl)propyl]-1,2-ethanediamine (DAMO).

7. The biochip according to claim 1, wherein the ionic liquid is formed by mixing an organic base with a Lewis acid.

8. The biochip according to claim 7, wherein the organic base is one selected from the group consisting of the following: 1-n-butyl-3-methylimidazolium (BMI), 1-octanyl-3-methylimidazolium (DMI), and 1-hexadecanyl-3-methylimidazolium (HDMI).

9. The biochip according to claim 7, wherein the Lewis acid is one selected from the group consisting of the following: $BF_4^-$, $PF_6^-$, $AsF_6^-$, $SbF_6^-$, $F(HF)_n^-$, $CF_3SO_3^-$, $CF_3CF_2CF_2CF_2SO_3^-$, $(CF_3SO_2)_2N^-$, $(CF_3SO_2)_3C^-$, $CF_3COO^-$, and $CF_3CF_2CF_2COO^-$.

* * * * *